(12) United States Patent
Kock et al.

(10) Patent No.: US 6,610,086 B1
(45) Date of Patent: *Aug. 26, 2003

(54) RADIALLY EXPANDABLE STENT IV

(75) Inventors: Wulf Kock, Alzenau (DE); Günter Herklotz, Bruchköbel (DE); Matthias Frericks, Hanau (DE); Jens Trötzschel, Bruchköbel (DE)

(73) Assignee: W. C. Heraeus GmbH & Co. KG, Hanau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/340,939

(22) Filed: Jun. 28, 1999

(30) Foreign Application Priority Data

Jul. 3, 1998 (DE) .................................. 198 29 701

(51) Int. Cl.⁷ .................................................. A61F 2/06
(52) U.S. Cl. ...................................... 623/1.22; 623/1.15
(58) Field of Search ............................ 623/1.15, 1.16, 623/1.22, 23.7; 606/195, 198

(56) References Cited

U.S. PATENT DOCUMENTS

| | | | |
|---|---|---|---|
| 4,969,458 A | | 11/1990 | Wiktor |
| 5,133,732 A | * | 7/1992 | Wiktor ........................ 606/195 |
| 5,405,377 A | * | 4/1995 | Cragg ......................... 623/1.22 |
| 5,800,526 A | * | 9/1998 | Anderson et al. ........... 623/1.16 |
| 5,843,168 A | * | 12/1998 | Dang ........................ 623/1.15 |
| 5,853,419 A | | 12/1998 | Imran |
| 6,042,597 A | * | 3/2000 | Kveen et al. ................ 606/198 |
| 6,066,169 A | * | 5/2000 | McGuinness ............... 623/1.16 |
| 6,117,165 A | * | 9/2000 | Becker ........................... 623/1 |
| 6,206,910 B1 | * | 3/2001 | Berry et al. ................. 623/1.15 |
| 6,264,688 B1 | * | 7/2001 | Herklotz et al. ........... 623/1.16 |
| 6,287,336 B1 | * | 9/2001 | Globerman et al. ........ 623/1.15 |

FOREIGN PATENT DOCUMENTS

| | | |
|---|---|---|
| EP | 0 335 341 A1 | 10/1989 |
| EP | 0 335 341 B1 | 3/1992 |
| EP | 0 873 728 A2 | 10/1998 |
| WO | WO 99/17680 | 4/1999 |

* cited by examiner

Primary Examiner—Paul B. Prebilic
(74) Attorney, Agent, or Firm—Akin Gump Strauss Hauer & Feld, L.L.P.

(57) ABSTRACT

A radially expandable support structure is presented, for keeping open lumina within a body, in particular a blood vessel, having a tube-shaped structure that has at least two partial structures, with a wall surface that extends between a first and a second end, which has several cut out areas, in particular, slits, which are essentially oriented parallel to the longitudinal axis of the tube-shaped structure. At least one of the partial structures (11) extend without interruption in the axial direction generally from the first end to the second end of the tube-shaped structure. A first partial structure (1, 2) can be expanded at least in the radial direction and has at least one radial-expansion component. The individual radial expansion components (12, 13) are arranged as a helix or in a helix shape. A second partial structure (11) is generally almost rigid in the axial direction. The two partial structures (1, 2; 11) are arranged in such a way that during the radial expansion of the tube-shaped structure, the second partial structure (11) receives the longitudinal axial forces that arise.

7 Claims, 1 Drawing Sheet

US 6,610,086 B1

RADIALLY EXPANDABLE STENT IV

BACKGROUND OF THE INVENTION

The invention involves a radially expandable support structure for keeping open lumina within a body, in particular a blood vessel.

EP 0 335 341 B1 discloses, among other things, an expandable intraluminar vascular structure or prosthesis having at least one thin walled tube-shaped part with first and second ends and a wall surface arranged between the first and second ends, which has essentially the same thickness and several slits, which are directed essentially parallel to the longitudinal axis of the tube-shaped part. The tube-shaped part can have a first diameter, which makes the intraluminary transport of the tube-shaped part into a body passage that has a lumen possible, and the tube-shaped part can have a second, expanded and deformed diameter; such that a force directed radially outwardly can be applied from inside of the tube-shaped part and the second diameter is variable and depends on the amount of the force acting on the tube-shaped part, whereby the tube-shaped part is expanded and deformed in order to expand the lumen of the bodily passage. The vascular structure or the vascular prosthesis has several tube-shaped parts and at least one connection piece, which is arranged between tube-shaped parts that border each other, in order to connect tube-shaped parts, which are bordering each other, together with each other in a flexible manner.

A disadvantage in this intraluminary vascular structure is the relatively high radial rigidity of the individual parts, which noticeably impairs the flexibility necessary in a lumen for the prevention of internal injuries.

In U.S. Pat. No. 4,969,458, an intraluminary support structure is disclosed, which is made up of a spiral-shaped spring. Disadvantageous in this is the relatively high radial instability, which can lead to positions of undesired buckling.

SUMMARY OF THE INVENTION

From the aforementioned stems the problem of at least partially eliminating the disadvantages mentioned above using a new type of support structure. The resulting problem lies in particular in ensuring a high stability in the longitudinal direction with not too small of a radial rigidity, while avoiding a shortening of the support structure during radial expansion and while avoiding uncontrolled radial buckling movements.

This problem is solved according to the invention by a support structure according to the present invention.

The support structure according to the invention has a tube-shaped body that has at least two partial structures, with a wall surface that extends between a first and a second end, which has several cut out areas, in particular, slits, which are essentially oriented parallel to the longitudinal axis of the tube-shaped body. At least one partial structure runs without interruption in the axial direction almost, at least, from a first end to a second end of the tube-shaped structure. The first partial structure can be expanded at least in the radial direction and has at least one radial-expansion component, where the individual radial expansion components are arranged as a helix or in a helix shape. The second partial structure is almost rigid in the axial direction. The radial expansion component can be constructed to be closed, for example, oval, rectangular, rhomboidal, or elliptical in shape, or open, for example, in a meandering shape.

Through in particular this arrangement of the partial structures, it is achieved that during the radial expansion of the tube-shaped body, the second partial structure receives the thereby arising longitudinal forces. This has the result that the radial deformation is independent of the axial deformation and accordingly no shortening in the longitudinal direction occurs during the radial expansion. This is especially important during the invasive surgery, in order to create a desired supporting effect over a certain length.

In an advantageous manner, at least one partial structure has at least one meandering pattern, in order to increase the flexibility. This applies for the at least two partial structures.

It is advantageous that the loops of the meandering pattern are of varying sizes. This involves the elongation (amplitude) and/or wavelength, both in the radial as well as in the longitudinal direction of the support structure. Thus, on the whole a highly homogenous expandability relative to the first partial structure arises.

Furthermore, it is advantageous that the meandering pattern is a double meandering pattern, in order to increase the radial expandability.

The double meandering pattern is made advantageously of a first meandering pattern having loops and a second meandering pattern having larger or smaller loops than that of the first meandering pattern, in order, in this manner, to achieve at least an approximately uniform expansion during loading to cause radial expansion.

Furthermore, in an advantageous manner, a connection element that connects to the respective longitudinal end of the first radial expansion component is constructed as a loop-shaped stay. The stay prevents or lessens the possibility of the loops becoming spaced apart or rising out of the surface of the support structure when bending is required. Furthermore, when expanded, they improve the support action of the stent via a uniform surface.

In addition, it is advantageous when the wall surface has an essentially uniform thickness, in order to improve the homogeneous radial expansion.

The support structure can, for example, be made of a stainless steel that is suitable for medical purposes and/or have a biocompatible coating. Furthermore, any biocompatible material can be used as a material for manufacturing the stent, for example, tantalum, platinum, niobium, alloys and synthetic materials. The structures can be manufactured by laser cutting, electro-erosion, etching or even metal cutting.

BRIEF DESCRIPTION OF THE SEVERAL VIEWS OF THE DRAWINGS

The foregoing summary, as well as the following detailed description of the preferred embodiment of the invention, will be better understood when read in conjunction with the appended drawings. For the purpose of illustrating the invention, there is shown in the drawing an embodiment which is presently preferred. It should be understood, however, that the invention is not limited to the precise arrangements and instrumentalities shown. In the drawings.

DETAILED DESCRIPTION OF THE INVENTION

Figure 1:
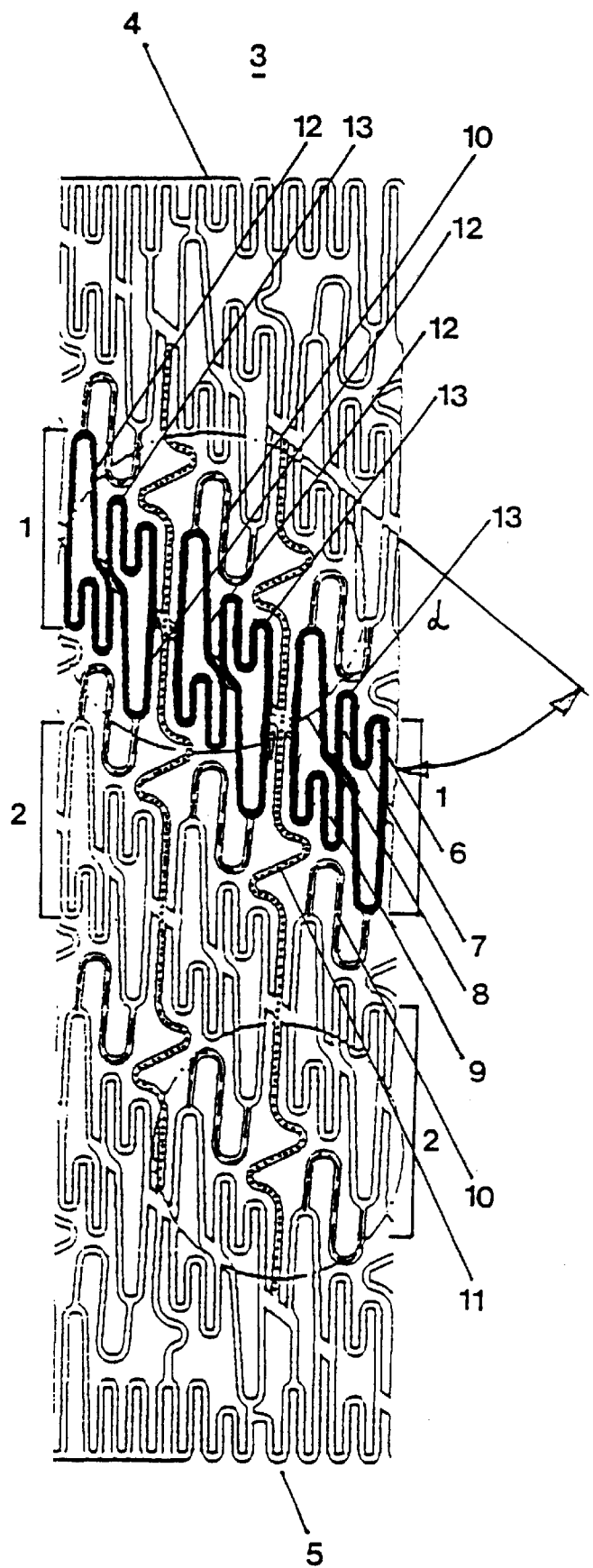
FIG. 1 is an unrolled support structure.

FIG. 1 shows the unrolled, wall surface of a support structure. This has a first partial structure 1, 2 that includes double meandering structures made up of meandering structures 12 and 13 and a second partial structure 11. The meandering structures form several slits 6, 7, 8, 9, which are directed essentially parallel to the longitudinal axis of the tube-shaped body 3. The second partial structure 11 runs without interruption in the axial direction almost from the first end 4 to the second end 5. The first partial structure can be expanded in the radial direction and has a radial expansion design element, which is made up of the radial expansion components 12, 13. These are arranged as helixes. The second partial structure 11 is relatively rigid in the axial direction in spite of the loop-shaped progression.

Furthermore, the connection element 10 that connects to the longitudinal ends of the radial expansion component 12, i.e. in this case on the loop ends of the first meandering pattern 12, is constructed as a loop-shaped stay.

The stent depicted as an example has a length of approx. 15 mm and a radial circumference of approx. 4 mm. The helix angle α of the helix amounts to approximately 50° relative to the longitudinal direction of the support structure.

With this exemplary embodiment of the support structure according to the invention, excellent results are achieved.

What is claimed is:

1. Radially expandable support structure for keeping open a lumen within a body comprising:

a tube-shaped body having two partial structures, the tube-shaped body having a wall surface extending between a first and a second end of the tube-shaped body, the wall surface having several cut out areas essentially oriented parallel to a longitudinal axis of the tube-shaped body, the at least two partial structures including a first partial structure (1, 2) being expandable at least in a radial direction and having at least one meandering pattern as a radial-expansion component, wherein individual radial-expansion components (12, 13) directly connected to each other from the first end (4) to the second end (5) of the tube-shaped body are arranged in an almost helical shape, and a second partial structure (11) being substantially rigid in an axial direction and extending without interruption in the axial direction generally from the first end to the second end of the tube-shaped body, the second partial structure (11) also having at least one meandering pattern, a portion of the second partial structure (11) being integral with the first partial structure (1, 2) intermediate the first and the second end of the tube-shaped body, the first and second partial structures (1, 2; 11) being such that each radial-expansion component (12, 13) radially succeeds a second partial structure (11) and that the second partial structure (11) receives longitudinal axial forces that arise during radial expansion of the tube-shaped body, wherein the radial deformation is independent from the axial deformation and no shortening in the longitudinal direction occurs during the radial expansion.

2. Support structure according to claim 1, wherein the loops of the meandering pattern are of variable sizes.

3. Support structure according to claim 1, wherein the meandering pattern is a double meandering pattern.

4. Support structure according to claim 3, wherein the double meandering pattern of the first partial structure (1, 2) consists of a first meandering pattern (12) with loops and a second meandering pattern (13) with larger or smaller loops in comparison to the loops of the first meandering pattern.

5. Support structure according to claim 4, wherein at least one connection design element (10), connected to respective longitudinal ends of the first meandering pattern (12), is constructed as a loop-shaped stay.

6. Support structure according to claim 1, wherein the wall surface has an essentially uniform thickness.

7. Support structure according to claim 2, wherein the meandering pattern is a double meandering pattern.

* * * * *